United States Patent [19]

Kopp et al.

[11] 4,219,530
[45] Aug. 26, 1980

[54] APPARATUS FOR ANALYZING BIOLOGICAL SPECIMENS

[75] Inventors: Reiner H. Kopp, Centerport; John Schmermund, Syosset, both of N.Y.

[73] Assignee: Brinkmann Instruments, Inc., Westbury, N.Y.

[21] Appl. No.: 872,824

[22] Filed: Jan. 27, 1978

[51] Int. Cl.² .................. G01N 33/16; G01N 31/06
[52] U.S. Cl. .................................. 422/69; 422/81; 422/101
[58] Field of Search ............. 422/82, 81, 70, 101, 422/69, 71

[56] References Cited

U.S. PATENT DOCUMENTS

| | | | |
|---|---|---|---|
| 3,097,927 | 7/1963 | Skeggs | 422/70 X |
| 3,098,719 | 7/1963 | Skeggs | 422/82 |
| 3,230,048 | 1/1966 | Skeggs | 422/70 |
| 3,373,872 | 3/1968 | Hrdina | 422/70 |
| 3,399,972 | 9/1968 | Skeggs et al. | 422/70 X |
| 3,649,203 | 3/1972 | Schneider | 422/81 |
| 3,826,615 | 7/1974 | Smythe et al. | 422/82 |
| 3,846,074 | 11/1974 | Tulumello et al. | 422/70 |
| 3,954,411 | 5/1976 | Snyder | 422/82 |

*Primary Examiner*—R. E. Serwin
*Attorney, Agent, or Firm*—Eisenman, Allsopp & Strack

[57] ABSTRACT

There is disclosed apparatus for automatically extracting compounds of clinical significance from a plurality of biological samples simultaneously by elution using a multi-channel system with common sources of wash reagents and eluent and common pre-programmed controls for all channels including means to purge wash and dry the channels between stages and means to inject essentially inert gas plugs as the interfaces between subsequent liquid phases. The extracted compounds can be mixed with reagents, mechanically agitated and examined qualitatively and/or quantitatively as by spectrophotometry to yield output readings for all channels. The flow patterns within the channels are determined by liquid-apportioning means and fluid distribution and metering, including both liquid and gaseous is accomplished by valves which respond to single control inputs to effect flow in all channels simultaneously.

19 Claims, 6 Drawing Figures

APPARATUS FOR ANALYZING BIOLOGICAL SPECIMENS

BACKGROUND OF THE INVENTION

The need for rapid, inexpensive and effective tests of large numbers of biological specimens for materials of clinical significance, such as steroids, hormones and drugs, has accelerated the evolution of new techniques and apparatus to supplant or improve upon the otherwise effective solvent-extraction thin-layer chromatography techniques of past years. Typically, improved results are achieved in one category, such as cost, by sacrificing another, such as scope of the analysis in terms of the number of the materials detected in any one analysis. Disposable cartridges using special adsorption resins and, more recently, the simultaneous testing of multiple pre-processed samples, have been evolved but none has freed the art of the need for more rapid, less expensive, and less labor-intensive procedures.

The present invention has for its objects to provide a system for automatically extracting compounds of clinical significance from biological samples and, further, for providing for the simultaneous extraction of these compounds and subsequent elution from a large number of biological specimens. Also provided are multi-channel valves and metering means for simultaneously controlling fluid flow, both liquid and gas, into and out of each channel from common control impulses derived from a programmed source.

THE PREFERRED EMBODIMENT

Figure 1:
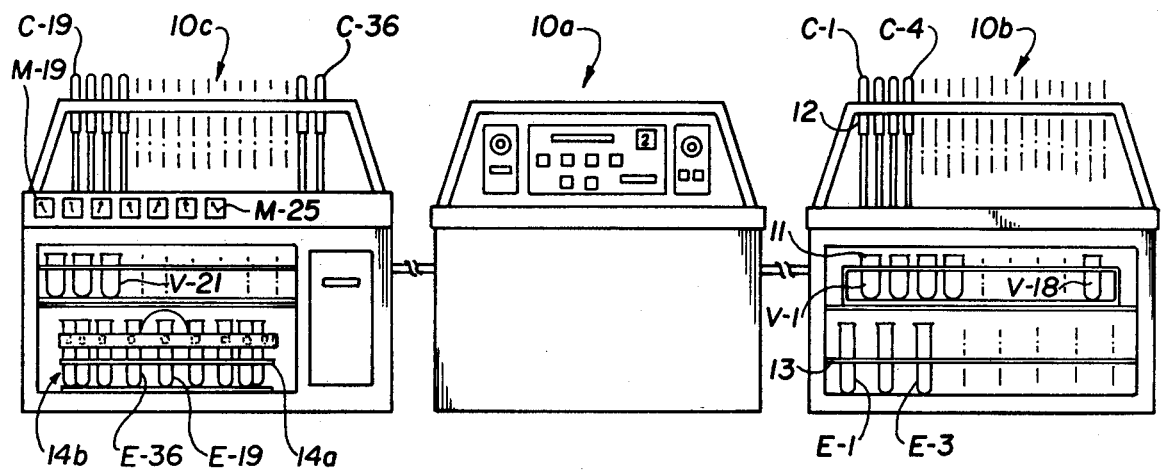
FIG. 1 is a view in perspective of the exterior of a complete processing apparatus, including a control console and a specimen-processing unit for isolating clinically significant compounds from a plurality of biological specimens at the same time and for furnishing a quantitative analysis of the compounds.

Referring to FIG. 1, the invention is illustrated as embodied in a system for simultaneously handling a plurality of biological specimens, for example, 36, at one time and, more particularly, for isolating from each of the specimens such compounds including drugs or steroids as might be present in the specimens. The basic processing apparatus takes the form of a control console or programming unit 10a, which can be arranged to handle up to 36 test channels, and a specimen-processing unit 10b, which can accommodate from 1 to 18 samples and components extracted therefrom. It will be understood that the two units can be either separated for convenience and cable-connected as shown or integrated in a single housing, and that 2 or more specimen-processing units can be operated from a single control console. In the arrangement of FIG. 1, the control consle 10a is coupled to a second unit 10c which performs, in addition to the specimen-processing functions of the unit 10b, the fully automated functions of quantitatively analyzing the extracted compounds.

The specimen-processing unit 10b includes a removable rack 11 which can hold a plurality of biological specimens such, for example, as 18 vials V-1, V-2 ... V-18 of urine; a fixed rack 12 for holding a corresponding plurality of expendable adsorption cartridges C-1, C-2 ... C-18 containing a permeable solid, such as a non-ionic resin, that will extract by adsorption compounds of interest from the specimens and of the type typically used in laboratory work for adsorbing organic molecules from aqueous solutions; and a removable rack 13 for holding the same number of eluent-collecting or final test vials E-1, E-2 ... E-18. Also included in the processing unit 10b are a plurality, 6 in this embodiment, of reservoirs R-1, R-2 ... R-6 for wash and elution reagents, not visible in FIG. 1 but shown diagrammatically in FIG. 2.

The units 10a and 10b are functionally an extraction device for isolating compounds of interest from the respective specimens. They do not yield the ultimate qualitative or quantitative data being sought, this being left to a laboratory technician who conducts the necessary analysis as by the use, for example, of standard chromatography or colorimetric procedures or a spectrophotometer. In accordance with the present invention, the final analysis procedures can also be automated. The unit 10c includes, in addition to the basic mechanism of the unit 10b, other reagent reservoirs R-7, R-8 and R-9 (not seen in FIG. 1 but shown in FIG. 2A) from which reagents are drawn in precisely metered proportions to be mixed with the extracted compounds in the collection vials E-19 ... E-36, preferably by ultrasonic vibrations. These vials are seated in an annular rack 14a of a light carrousel 14b forming part of a multi-channel spectrophotometer 14 (shown schematically in FIG. 2A and described more fully below) which can include as its readout means individual meters M-1, M-2 ... M-18 supplemented, if desired, by automatic printout means.

Figure 2:
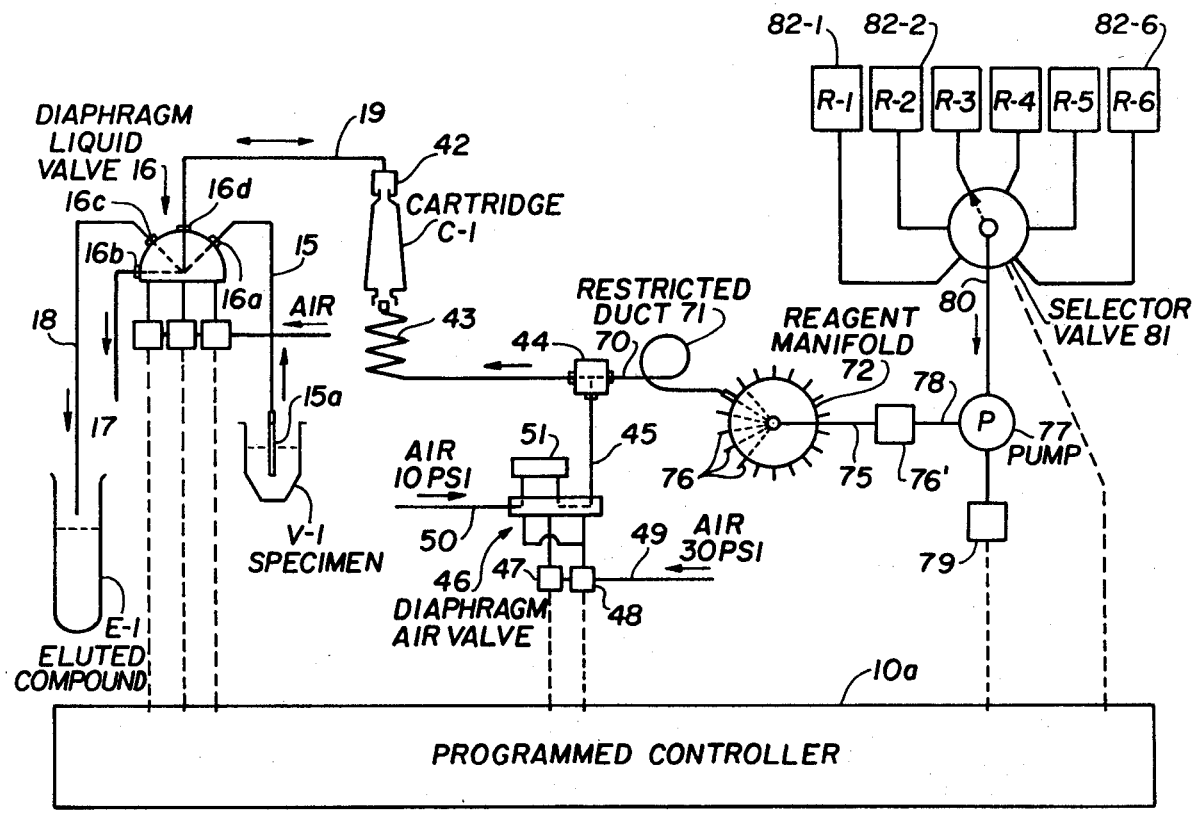
FIG. 2 is a simplified schematic diagram of one of the plurality of identical sampling sections in the processing unit of FIG. 1.
Figure 3:
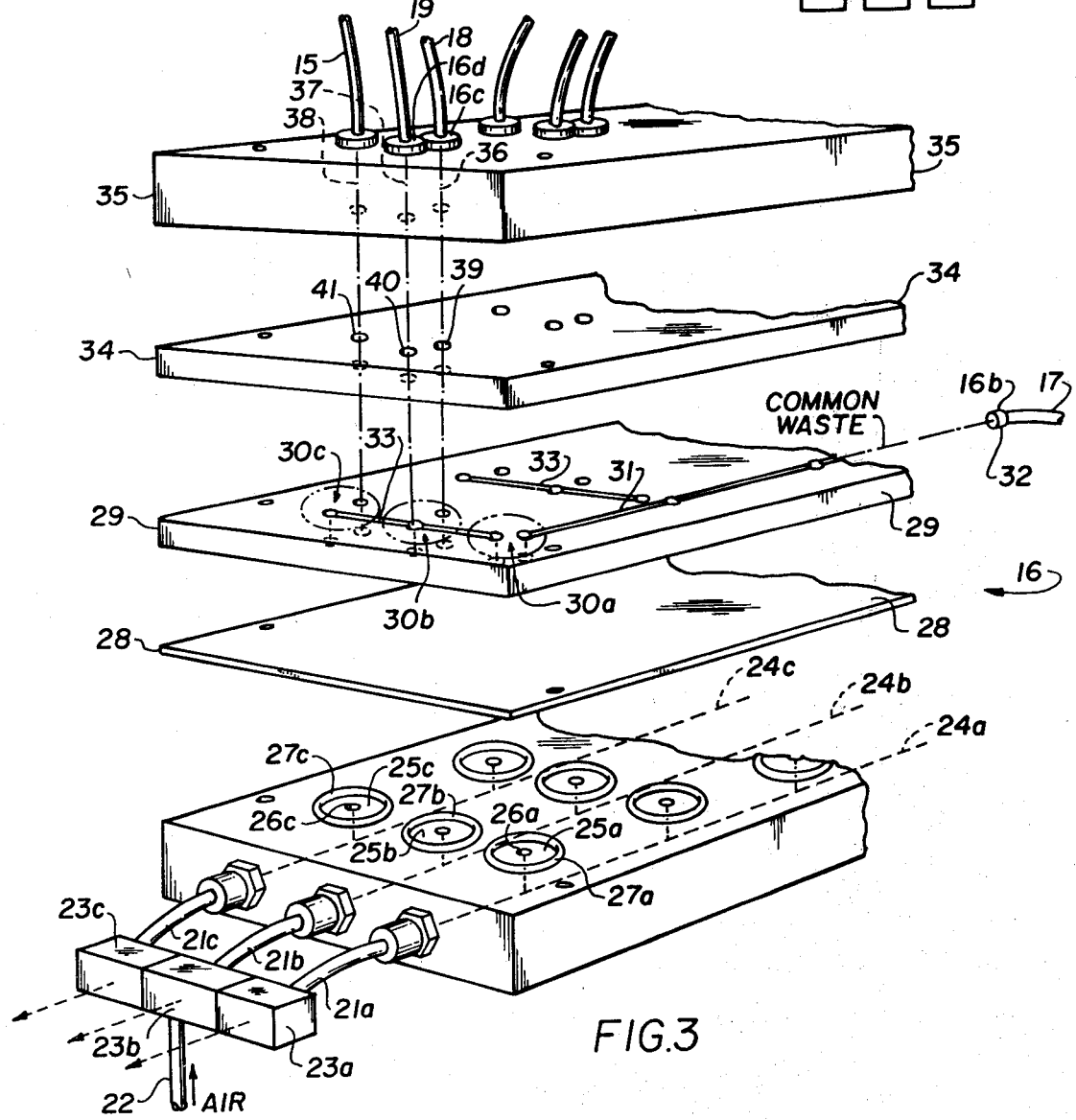
FIG. 3 is an exploded fragmentary view in perspective of a diaphragm valve for multi-liquid control in the multiple channels of the system.

The control console 10a includes essentially all of the control mechanism for the system including flow rate controls, timing controls, slots for receiving interchangeable program cards, function indicators, alarms and the like, all of which control and interact with the specimen-processing system best understood by reference to FIG. 2, in which there is shown schematically one complete channel of the 18-channel specimen-processing unit 10b, and in which the 18 channels operate concommitantly in parallel. The specimen vial V-1 is entered by a sample uptake tube 15 which includes a replaceable polypropylene tip 15a with a cotton filter to remove any precipitate contained in the specimen. The uptake tube 15 leads to the first port 16a of a three-way diaphragm operated valve assembly 16 particularly adapted for the control of various liquids in a plurality of channels simultaneously and the details of which are shown in FIG. 3. The diaphragm valve 16, which is common to all 18 channels, also includes a waste-line port 16b connected to a waste line 17 and an elution port 16c connected to an elution output line 18 leading to the vial E-1, and a common port 16d connected by a conduit 19 to the adsorption cartridge C-1 removably seated in its rack or cartridge station 12 (FIG. 1).

The diaphragm valve 16 operates under the control of the console 10a from a source of air pressure as a three-way distribution valve in which the common port is constantly open to the conduit 19. The broad function of this valve is to implement the withdrawal of biological samples of the specimens from the vials V-1 . . . V-18, subjecting the samples to adsorption within the cartridges C-1 . . . C-18 (in one or more passes) of compounds of interest therein, and extracting the compounds from the adsorption cartridges C-1 . . . C-18 by means of the reagents in the reservoirs R-1 . . . R-5, for collection in the eluent containers E-1 . . . E-18, the latter cycle being interspersed with various conduit clearing and cleaning cycles.

FIG. 3 shows, in an exploded view, a portion of the three-way diaphragm valve 16 to the extent of two of the eighteen channels. It will be understood that the other sixteen channels are duplications extending along the length of the unit. The assembly includes a manifold base 20 having three service air conduits 21a, 21b and 21c coupled to its end and fed by a source of air under pressure from a common conduit 22 which branches through three solenoid-operated air valves 23a, 23b and 23c, each connected electrically to the control unit 10a (FIGS. 1 and 2) and operable individually. When open, air pressure is impressed on the respective associated conduits; when closed, the conduits are connected to atmospheric or sub-atmospheric pressure. The conduits 21a, 21b and 21c are respectively connected to longitudinal ducts 24a, 24b and 24c in the body of the manifold 20. Formed in the upper surface of the manifold 20 are eighteen groups of three transversely aligned cylindrical recesses, only two of which are shown in the fragmentary view of FIG. 3. The recesses 25a, 25b and 25c are associated with the first channel and are respectively connected to the longitudinal ducts 24a, 24b and 24c by ducts 26a, 26b and 26c. O-rings 27a, 27b and 27c are seated in the recesses. Above the manifold 20 and normally pressed tightly thereagainst is a flexible imperforate membrane diaphragm 28 which is common to all valves in the unit. Pressed tightly against the other side of the diaphragm 28 is a valve body 29 through which pass, for each channel, three duct pairs 30a, 30b and 30c. The duct pairs 30a terminate above the recess 25a on the upper side of the diaphragm 28; the duct pairs 30b above the recess 25b; and the duct pairs 30c above the recess 25c. The diaphragm will press upwardly against the duct pairs 30a, 30b and 30c on the underside of the valve body in air-tight relationship when air pressure is applied from below but, when the pressure on the underside of the diaphragm is relatively less than that on the upper side, the diaphragm will flex into the recesses to place the respective duct pairs in communication with each other on the underside of the valve body. Formed in the upper surface of the valve body is a groove 31 extending along the length thereof and terminating in a fitting 32 connected to the duct 17 which is the waste line in FIG. 3. The groove 31 connects one of the ducts in the pair 30a of the first channel and each of the corresponding ducts of the other seventeen channels. Also formed in the upper surface of the valve body are eighteen transverse grooves 33, each joining one of the ducts of the pair 30a with a corresponding duct in each of the pairs 30b and 30c.

The assembly is completed by a sealing plate 34 which can be formed of plastic, such as polypropylene, with a glass filler and which, when pressed against the metal valve body, effectively seals against lateral leakage between all duct terminations except those connected by grooves. The sealing plate 34 is held in place by a connector plate 35 having on its upper surface fittings to which the sample conduit 15, the cartridge conduit 19, and the elution conduit 18 of the first channel are connected, it being understood that similar groups of three conduits are connected for each of the other seventeen channels. The connector plate 35 is pierced by ducts 36, 37 and 38, and the sealing plate 34 is pierced by ducts 39, 40 and 41, so aligned that the cartridge conduit 19 and the elution conduit 18 connect to the ducts of the pair 30b. The sample conduit 15 is connected by a single duct sequence through the connector plate and sealing plate to a point above the recess 25c.

It will be understood, therefore, that when air pressure is introduced into each of the recesses 25a, 25b and 25c under the control of the solenoid valves 23a, 23b and 23c as actuated from the control unit 10a, all of the flow paths will be closed by virtue of the diaphragm 28 pressing tightly against the underside of the valve body for all channels. By selective actuation of the solenoid valves to release the air pressure in one or more of the recesses 25a, 25b and 25c, the conduit 19 from the cartridge C-1 can be connected either to the specimen vial V-1 through the conduit 14, to the eluent collector vessel E-1 by conduit 19, or to the waste line by conduit 17, and all channels will operate in parallel. The diaphragm will flex downwardly within the O-ring 27b to connect the duct pairs 30b so that the liquid passing through the cartridge C-1 will be passed into the eluent vessel E-1. It will be apparent, therefore, how the respective parts of the diaphragm valve 16 operate as the sequence of operations of the system is carried out.

Figure 4:
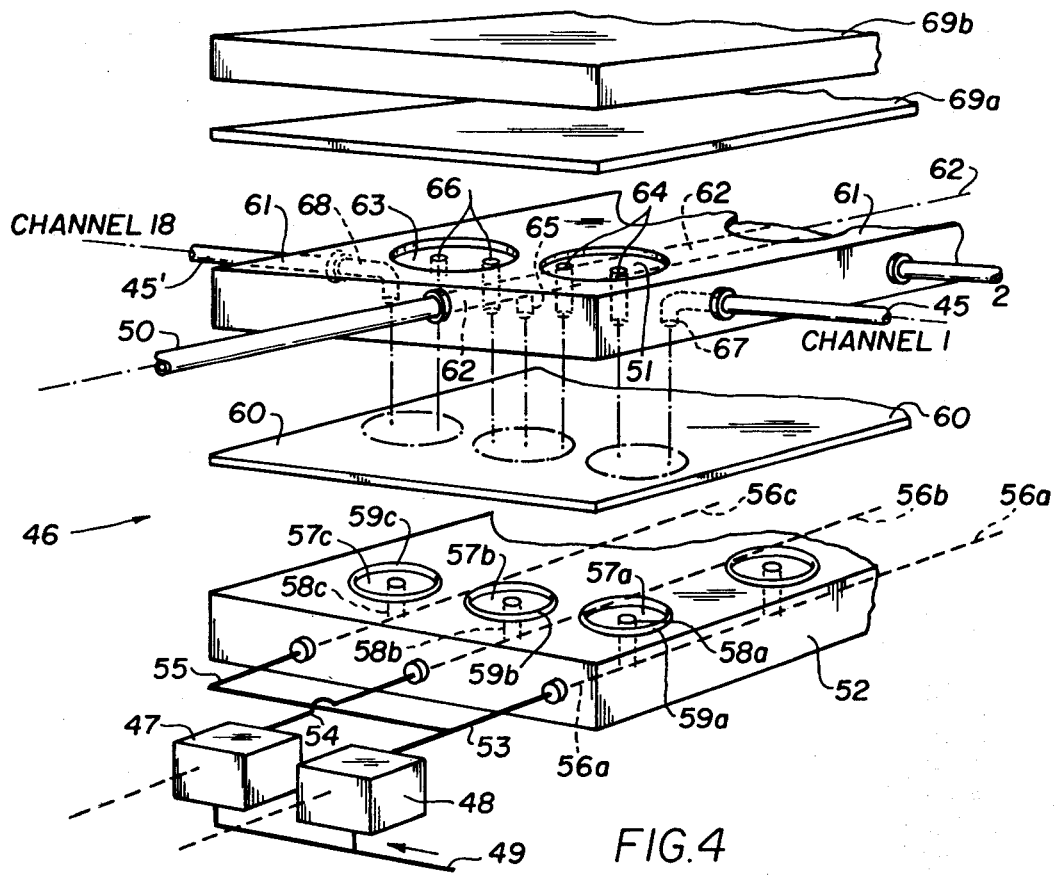
FIG. 4 is an exploded fragmentary view in perspective of a diaphragm valve which controls and meters air.

Referring again to FIG. 2, the cartridge C-1 is detachably mounted in a support, the upper end 42 of which is connected to the conduit 19 and the lower end of which comprises a storage reservoir in the form of a coil 43 having a capacity normally exceeding the volume of the specimen being tested. Thus, fluids, liquid or gaseous, can flow in either direction through the cartridge. The other end of the storage coil 43 is connected to a liquid tee block 44 which is preferably an elongated block having eighteen tee connections therein. The second connection to the tee 44 is an air conduit 45 which leads to an air controlling and metering diaphragm valve assembly 46, the broad functions of which are to selectively inject air continuously into the system, or to inject into the lines of each channel metered volumes of air to constitute air interface plugs between different liquids flowing in series in the channels. The illustration of the air diaphragm valve 46 in FIG. 2 is schematic in nature and shows a single channel. The structural details of a single valve unit for all channels are shown in FIG. 4. The diaphragm valve includes a pair of solenoid-actuated air valves 47 and 48, each fed by a conduit 49 to a high pressure air source and connected individually for selective actuation to the program and control unit 10a. The diaphragm valve is also connected by a conduit 50 to a low pressure air source from which is derived the air for insertion into the respective channels of the system. Also contained within the body of the diaphragm valve 46 is a metering chamber 51 for each of the eighteen channels.

The fundamental design of the diaphragm valve is similar to that of the diaphragm control liquid valve of FIG. 3. It includes a manifold base 52 having three service or control air conduits 53, 54 and 55 connected to its end from the solenoid valves 47 and 48. The conduits 53 and 55 are tied together in parallel. The conduits 53, 54 and 55 are respectively connected to longitudinal ducts 56a, 56b and 56c extending the length of the manifold base. Eighteen groups of three transversely aligned cylindrical recesses 57a, 57b and 57c are formed in the upper surface of the manifold 52, only one group of which is shown in FIG. 4, and the recesses are respectively connected by transverse ducts 58a, 58b and 58c to the longitudinal ducts 56a, 56b and 56c. O-rings 59a, 59b and 59c are seated in the recesses and a flexible membrane diaphragm 60 is pressed tightly aginst the upper surface of the manifold 52 sealing the respective recesses to define chambers in which the diaphragm flexes under the control of air controlled by the solenoids 47 and 48. Pressed against the upper surface of the diaphragm 60 is a valve body 61 which has a central longitudinal duct 62 formed therein and connected at one end to the air conduit 50 leading to the low pressure air source. The assembly is completed by a top plate 69b and a sealing gasket 69a. Two rows of nine recessed cavities each are formed in the upper surface of the valve body 61, only two of which are shown in FIG. 4. The cavity 51 (also identified schematically in FIG. 2) is associated with the first channel of the system. A second cavity 63 is also shown, this being associated with the eighteenth channel of the system. A first duct pair 64 pass vertically from the cavity 51 to the opposite side of the valve body with one duct terminating above the recess 57a on the opposite side of the diaphragm 60 and the other above the recess 57b. A single transverse duct 65 connects the longitudinal duct 62 to a point above the recess 57b and a duct pair 66 connects the cavity 63 to points respectively above the recesses 57b and 57c. A short transverse duct 67 joins the conduit 45 at the side of the valve body (and connected at its other end to the liquid tee 44 of FIG. 2) with a point above the recess 57a. Similarly, a conduit 68 is connected from a point above the recess 57c to a conduit 45 also leading to the liquid tee 44 and representing the eighteenth channel of the system.

In operation, with the solenoid valves 47 and 48 actuated to admit high pressure air to the conduits 53, 54 and 55, the diaphragm 60 will seal tightly against the underside of the valve body to close all passages. When the solenoid valve 47 is closed to vent the recess 56b to atmosphere, the diaphragm 60 will be pressed into the recess 57b to admit air from the low pressure source in the conduit 50 and in the longitudinal conduit 62 and transverse conduit 65, to the newly created space above the diaphragm. Thus, low pressure air flows into all cavities including 51 and 63 on the upper side of the valve body, these volumes of air, however, being trapped therein because of the air pressure beneath the diaphragm in the recesses 57a and 57c. When it is desired to insert air continuously into any of the channels, the solenoid valve 48 is opened, allowing the diaphragm to depress in the recesses 57a and 57c, thereby opening a direct flow into the conduits 45 and 45. When it is desired to inject a metered plug of air into the channels, the solenoid 48 is first actuated to depressurize the recess 57a and the solenoid valve 47 is immediately actuated to introduce pressure into the recess 57b, thereby shutting off the continuous flow of air and allowing the metered volumes in the cavities of the valve body to flow into the respective channels.

Figure 5:
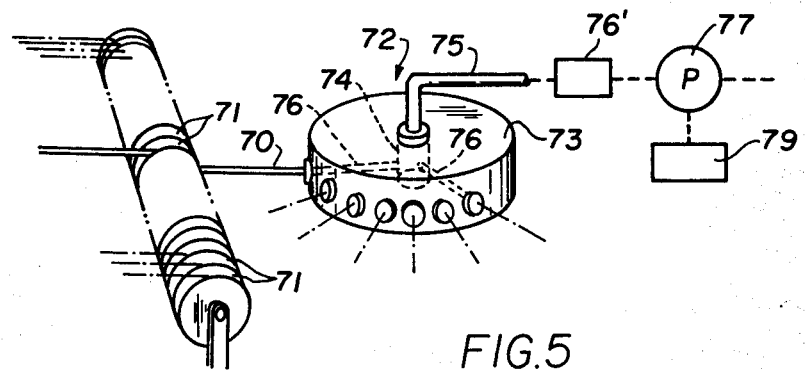
FIG. 5 is a top view, diagrammatic in nature, showing the multi-channel manifold and pumping unit for delivering simultaneously a plurality of equal charges of liquid.

Referring again to FIG. 2, the third limb from the liquid tee is a capillary tube 70 of extended length and which can be spooled as shown at 71 with its other end being connected to a solvent manifold 72, also shown in FIG. 5. The manifold 72 includes a generally cylindrical body 73 having a short axial bore 74 entered by a solvent conduit 75. A plurality of eighteen radial bores 76 join the axial bore 74 to the outer surface of the manifold, at which point they are connected to the capillary tube 70, one of which is provided for each of the eighteen channels (only one being shown in FIG. 5).

The solvent conduit 75 passes through a two-way distribution valve or tee 76' to a pump 77 through a single conduit 78. The pump 77 is controlled from the control unit 10a and preferably includes a precise regulator in the form of a feedback tachometer circuit 79, so that constant volume output is achieved for a wide range of liquids. The pump 77 also includes reversing controls connected to the control unit 10c to reverse the direction of flow in the system when desired, for example, to draw a sample from the specimen into the storage coil 43. The input to the pump 77 is through a conduit 80 leading to a rotary selector valve 81 as the common output thereof and which has as its input six conduits leading to six reagent reservoirs 82-1 . . . 82-6, which can contain, for example, wash reagents and eluents for use in the system, both for extracting compounds from the cartridges C-1 . . . C-18 and for washing the channels between steps. The rotary valve 81 is also connected to the control unit 10a for selection of the appropriate liquid.

The electronic circuits in the control unit 10a is basically a programmer and sequencer to control the rotary valve 81, the diaphragm valve 16 for the three-way distribution of liquids, the diaphragm valve 46 for injecting and metering air into the system, and the speed control circuit for the regulator of flow rate from the pump. An interchangeable rotary drum (not shown) that activates a switch provides a series of pulses at timed intervals during operation. Each pulse advances a stepping switch one position to control another event. Differing sequences are established by program cards which can be changed for each procedure. The tachometer feedback speed control circuit 79 produces a constant flow from the pump. Any variation in load due to a viscosity change in the liquid being pumped through the system is monitored by a tachometer and appropriate compensation will be introduced. At the end of the entire procedure, the stepping switch automatically resets so that another cycle can be repeated. A manual override can bypass the program when required for a modified procedure.

In the operation of the system as thus far described, samples can be processed to furnish automatically eluted compounds from the specimens under test. While the process is described below for one channel, it will be understood a plurality of up to eighteen duplicate and parallel tests can be carried out. A sample from the specimen vial V-1 in the rack 11 is, by appropriate actuation of the pump 77 and setting of the diaphragm valve 16 (to connect conduits 15 and 19), drawn through conduits 15 and 19 and through the cartridge C-1 into the holding coil 43. The large capacity of the holding coil plus the timing of the cycle precludes flow of the specimen beyond the holding coil. The amount of liquid from the specimen necessary to reach the liquid tee 44 is based on a timing function, it having been previously determined by the technician operating the system how much time is required to draw a volume of the sample from the vials to the liquid tee. The next stage of the operation as fixed by the program is to reverse the flow of the specimen from the holding coil back through the cartridge to once again expose it to the adsorption action of the resin particles in the cartridge. The specimen can be cycled back and forth to the cartridge as many times as the test procedure might call for, with two passes being sufficient for many procedures.

In the next step, the rotary valve 81 is turned to draw from the reservoir 82-1 which can be, for example, a water reservoir, and operating the pump 77 to drive water back through the system including the capillary tube 70, the liquid tee 44, the holding coil 43 and cartridge C-1 to the liquid diaphragm valve 16 which has been previously set by the program to discharge from the waste line 17. Any number of wash cycles can be carried out in order to clear the lines and manifolds of contaminants.

At this point in the cycle, all of the contaminants to be studied later are entrapped in the cartridges C-1 . . . C-18, and a second reagent from the reservoir 82-2 such, for example, as sodium hydroxide, is back-flushed through each of the channels into the cartridges C-1 . . . C-18 to the common waste line 17. A final water wash from reservoir 82-1 is then introduced through the cartridges to the waste line, after which the cartridges with any charges of contaminants which they might have in them, are ready for the elution phase. As a preliminary to the elution phase or, if desired, any stage in between, the liquid tee 44, the holding coil 43, the cartridge C-1 and conduit 19 are air-aspirated to remove the water, this being accomplished by the program which connects the air source to the air diaphragm valve 46 which blows air continuously from the source through the system. The elution operation is begun by operation of the selector valve 81 to the eluting or organic reagent in, say, the reservoir 82-3, which solution is driven by the pump 77 and through the various conduits to the respective holding coils 43. The capacity of the holding coils is such that it exceeds comfortably the volume of the eluting reagent required for the test procedure, and the volume is effectively controlled to be equal in all channels by means of the manifold 72 and the long capillary tubes fed thereby. When the precise amount of reagent is in the holding coils 43, a metered air plug is injected behind it. The latter is derived from the chamber 51 of the diaphragm valve 46 as described above.

With the eluting reagent thus isolated, the rotary valve 81 is turned back to reagent reservoir 82-1 containing water, and the liquid diaphragm valve 16 is operated to connect each of the cartridges C-1 through conduits 19 and 18 to elution or collection vessels E-1. The pump 77 forces water through the channel behind the metered air plug to drive the reagent through the cartridge where, as an organic solvent, it takes from the resin particles all of the contaminants therein and drives the material into the respective collection vessel E-1. In this fashion, a precisely known predetermined volume of organic reagent will be contained in the collection vials so that subsequent tests, such as standard chromatography tests, can be set into motion.

Figure 2A:
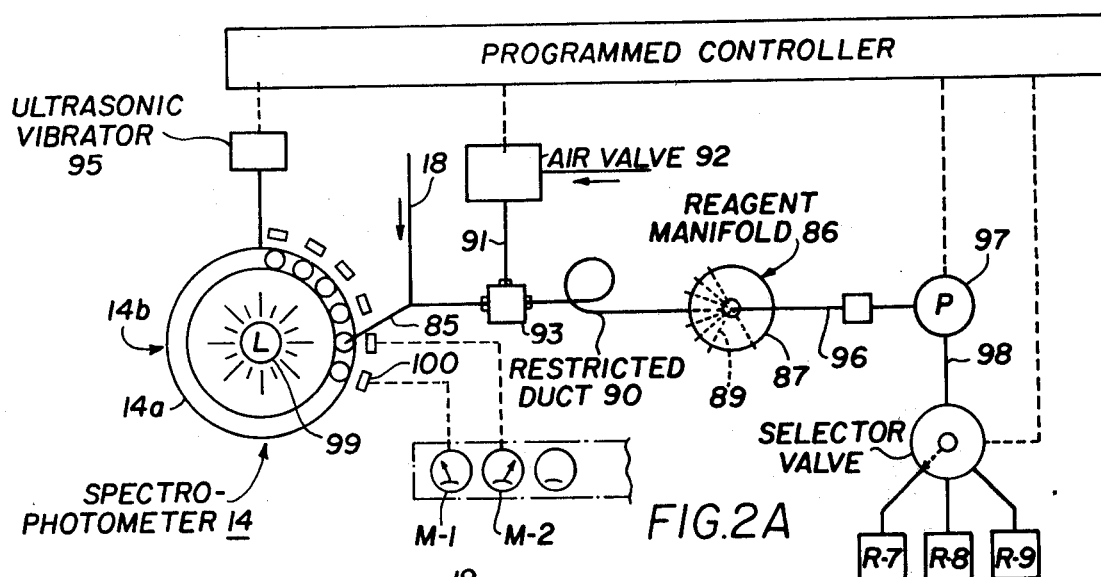
FIG. 2A is a schematic diagram of the system for effecting quantitative analysis.

The system as described leaves to a technician the final steps of processing the material in the vessels E-1 . . . E-18 to determine if certain compounds under investigation are present and, if present, the concentration thereof. In accordance with the present invention, the final stages of qualitative and/or quantitative testing can be performed automatically. FIG. 2A is a schematic diagram of such apparatus in the form of a continuation of the processing system of FIG. 2, with the complete system being disposed in the unit 10c. This unit, which is also a satellite of the basic control unit 10a, includes all of the basic system of the processing unit 10b but with conversion of the rack for holding the final test vials, in this case identified as E-19 . . . E-36, into a carrousel spectrophotometer. The eighteen vials are arranged in the light carrousel 14b beneath the elution conduits 85 representing the final output of the extraction phase. Precisely metered volumes of the desired reagent are injected into the vials from the distribution manifold 86 which can take the form of the manifold 72 of FIG. 2, including a cylindrical housing 87 having a short axial bore 88 tapped by smaller diameter radial bores 89 (in this case also eighteen in number) to each of which is connected a long capillary tube, all preferably spooled for convenience of storage and terminating at the output end in a storage reservoir 90, which can take the form of a holding coil elevated above the pumping channel. An air line 91 controlled by a valve assembly 92 is coupled into the line in a tee 93 at the input to the reservoir for discharging pneumatically the metered charge of reagent into its designated vial by means of a discharge nozzle. The reagent, after being discharged into the respective vials, is mixed with the materials therein by means of an ultrasonic vibrator 95 coupled to the circular mount in which the vials are tightly secured.

The input to the metering manifold is a single conduit 96 leading to the output of pump 97 which can be similar to the pump 77, and speed controlled by a tachometer feedback to furnish uniform output. The input to the pump is through a conduit 98 from a power-driven selector valve coupled to a series of reagent reservoirs R-7, R-8 and R-9, including wash water as well as test reagents as might be required for the particular test being performed. The selector valve, pump, air service and vibrator are all operated from the control unit 10a in the desired sequence.

A calibrated light source 99 is disposed in the center of the circularly mounted vials E-19 . . . E-36, and disposed radially outwardly of the respective vials from the central light source are a plurality of photoresponsive cells 100 connected to meters M-1, . . . M-18 on the housing of the unit 10c. The spectrophotometer thus formed can be calibrated by conventional means.

While the invention has been described above having reference to preferred embodiments thereof, it will be understood that it can take other forms and arrangements within the scope of the invention. For example, the restrictor formed by the capillary tubes 71 in the solvent manifold 72 and pump assembly 77 can be formed by means of metering orifices, bead restricted conduits, metering valves or membrane filters. Alternatively, controlled rate parallel path pumps, such as peristaltic valves, can be used. The diaphragm actuated pumps 16 and 46, while shown as formed of flat plate members, can take other configurations, such as cylindrical. The invention should not, therefore, be regarded as limited except as defined in the following claims:

We claim:

1. Apparatus for simultaneously extracting compounds from a plurality of specimens comprising
   (a) means defining a plurality of test channels each accommodating a charge of liquid permeable adsorptive material, (b) means to draw individual samples from a plurality of liquified test specimens respectively into the channels, (c) means to effect at least one pass of each sample through the charge of adsorptive material in the associated channel, (d) a liquified solvent reagent source including means to divide the reagent into a plurality of substantially equal predetermined volumes for passage through the respective charges of exposed adsorptive material to extract the accumulated compound therefrom, and (e) means to collect respective volumes of exposed reagent.

2. Apparatus as set forth in claim 1, said means to divide the reagent into a plurality of measured volumes comprising restrictor means in each channel.

3. Apparatus as set forth in claim 2, said restrictor means being selected from among capillary tubing, bead-restricted conduits, metering orifices, metering valve means, and membrane filter means.

4. Apparatus as set forth in claim 1, said means to divide the reagent into a plurality of measured volumes comprising controlled flow rate pump means in each channel.

5. Apparatus as set forth in claim 2, said restrictor means to divide the reagent into measured volumes comprising a cylindrical manifold having a central bore to receive reagent from the source, a plurality of radial bores joining the central bore to the perimeter and a plurality of capillary tubes respectively connected in series between the channels and the radial bores.

6. Apparatus as set forth in claim 5, said capillary tubes being long in relation to the radial bores and respectively spool mounted adjacent the cylindrical manifold.

7. Apparatus as set forth in claim 5, including motor-driven pump means connected in series to discharge reagent into the central bore of the manifold, means to selectively reverse the pumping direction, and feedback control means to regulate the pumping rate.

8. Apparatus as set forth in claim 1, said adsorptive material being carried in expendable cartridges, each of said channels including a releasable cartridge mount having in series therewith a holding reservoir having a capacity exceeding the volume of the sample.

9. Apparatus as set forth in claim 8, including distribution valve means operative for all channels and having one conduit connected to the cartridge mount and two selectively operable conduits connected respectively to the test specimens and the means to collect the volumes of exposed reagent.

10. Apparatus as set forth in claim 9, including a third selectable conduit in said distribution valve means connected to a waste line.

11. Apparatus as set forth in claim 2, including gas injection valve means connected to each channel between the restrictor means and the charge of adsorptive material.

12. Apparatus as set forth in claim 11, said gas injection valve means including means to inject gas continuously into each channel and selectively to inject metered volumes of gas into each channel to form a gas plug for the isolation of different serially flowing liquids in the channels.

13. Apparatus as set forth in claim 12, said reagent source including a plurality of reagent reservoirs and selector valve means operative for all channels and having input means connected to each of said reagent reservoirs, and output means connected to the respective channels.

14. Apparatus as set forth in claim 13, including distribution valve means connected to adsorptive charge of each channel and to the sample source and the means to collect exposed reagent; and program control means connected to said selector valve means and to said distribution valve means, whereby the system can sequentially and automatically extract samples of specimens, expose the samples to the adsorptive material in one or more passes, liquid wash the system, dry the system, expose the adsorptive material to solvent reagents, deposit the exposed reagents in collecting vessels, and purge, clean and dry the system.

15. Apparatus as set forth in claim 1, including
(a) means to add a reagent in a precise proportion to the respective eluted components,
(b) means to agitate the mixture, and
(c) means to subject the mixture in each channel to analysis.

16. Apparatus as set forth in claim 15, including means to flush the system.

17. Apparatus to divide a liquid into a plurality of units of substantially equal volume, comprising
(a) a manifold,
(b) a plurality of parallel channels connected to the manifold, and
(c) restrictor means in each of said channels.

18. Apparatus as set forth in claim 17, said manifold comprising a substantially cylindrical member having an axial volume to receive the liquid to be divided, a plurality of radial channels extending radially outwardly from the axial volume, and a plurality of restricted conduits connected respectively to the radial channels.

19. Apparatus according to claim 18, including a pump to introduce the liquid into the axial volume.

* * * * *

UNITED STATES PATENT OFFICE
CERTIFICATE OF CORRECTION

Patent No. 4,219,530　　　　　　　Dated August 26, 1980

Inventor(s) Reiner H. Kopp and John Schmermund

It is certified that error appears in the above-identified patent and that said Letters Patent are hereby corrected as shown below:

Col. 4, line 29, "conduit 19" should be --conduit 18--.

" 5, " 41, "45" should be --45'--.

" 5, " 48, "recess 56b" should be --recess 57b--.

" 5, " 61, the second "45" should be --45'--.

Signed and Sealed this

Twenty-fifth Day of November 1980

[SEAL]

*Attest:*

SIDNEY A. DIAMOND

*Attesting Officer*　　*Commissioner of Patents and Trademarks*